(12) United States Patent
Hagg et al.

(10) Patent No.: US 8,083,493 B2
(45) Date of Patent: Dec. 27, 2011

(54) TRANSPORT DEVICE FOR STERILE MEDIA

(75) Inventors: Martin Hagg, Wannweil (DE); Ralf Kuhner, Stuttgart (DE)

(73) Assignee: ERBE Elektromedizin GmbH, Tübingen (DE)

( * ) Notice: Subject to any disclaimer, the term of this patent is extended or adjusted under 35 U.S.C. 154(b) by 1140 days.

(21) Appl. No.: 10/573,767

(22) PCT Filed: Aug. 24, 2004

(86) PCT No.: PCT/EP2004/009451
§ 371 (c)(1),
(2), (4) Date: Mar. 29, 2006

(87) PCT Pub. No.: WO2005/034777
PCT Pub. Date: Apr. 21, 2005

(65) Prior Publication Data
US 2007/0129680 A1   Jun. 7, 2007

(30) Foreign Application Priority Data

Sep. 30, 2003 (DE) .................... 103 45 382
Oct. 21, 2003 (DE) .................... 103 48 832

(51) Int. Cl.
*F04B 41/06* (2006.01)
(52) U.S. Cl. .................. 417/8; 417/2; 417/62
(58) Field of Classification Search .......... 417/2, 8, 417/62, 216, 286, 426
See application file for complete search history.

(56) References Cited

U.S. PATENT DOCUMENTS

| | | | |
|---|---|---|---|
| 4,137,011 A | 1/1979 | Rock | |
| 4,527,954 A * | 7/1985 | Murali et al. | 417/46 |
| 4,543,044 A * | 9/1985 | Simmons | 417/342 |
| 4,635,621 A * | 1/1987 | Atkinson | 601/161 |
| 5,339,131 A * | 8/1994 | Rosenburgh et al. | 396/632 |
| 6,216,573 B1 * | 4/2001 | Moutafis et al. | 83/177 |
| 2002/0045912 A1 | 4/2002 | Ignotz | |
| 2003/0012660 A1 * | 1/2003 | Ishimoto | 417/223 |

FOREIGN PATENT DOCUMENTS

| | | |
|---|---|---|
| CN | 2213530 Y | 11/1995 |
| CN | 2213530 Y | 11/1995 |
| DE | 42 00 976 | 8/1995 |
| EP | 0 212 728 | 3/1987 |
| EP | 0 470 781 | 2/1992 |
| EP | 0 623 842 A1 | 11/1994 |

(Continued)

OTHER PUBLICATIONS

European Office Action dated Dec. 27, 2006.

(Continued)

*Primary Examiner* — Charles Freay
*Assistant Examiner* — Patrick Hamo
(74) *Attorney, Agent, or Firm* — Dickstein Shapiro LLP

(57) ABSTRACT

For water-jet surgery pump devices are known by means of which a sterile fluid is transported through a reservoir to the surgical instrument by means of piston pumps or similar volumetrically transporting pumps. In accordance with the present invention it is proposed either to construct drive means for the pumps in such a way that their suction cycle is shorter than the output cycle, or to provide a pump with at least three pump chambers and to construct the drive means in such a way that the suction and output cycles of the pump chambers overlap one another.

21 Claims, 3 Drawing Sheets

FOREIGN PATENT DOCUMENTS

| | | | |
|---|---|---|---|
| FR | 2 722 840 | | 1/1996 |
| FR | 2722840 | * | 1/1996 |
| JP | 6-332139 A | | 12/1994 |
| WO | WO 99/33510 | | 7/1999 |
| WO | WO 02/50197 | | 6/2002 |

OTHER PUBLICATIONS

Chinese Office Action dated Aug. 25, 2010, issued in related Chinese Application No. 200810181733 4.

* cited by examiner

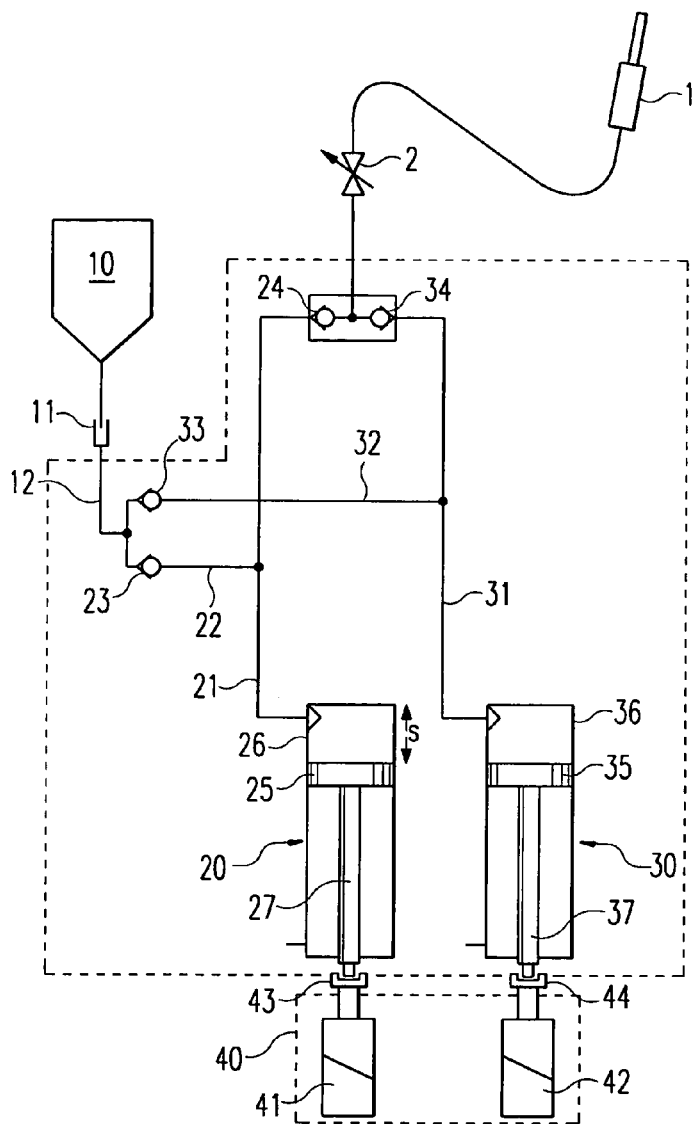
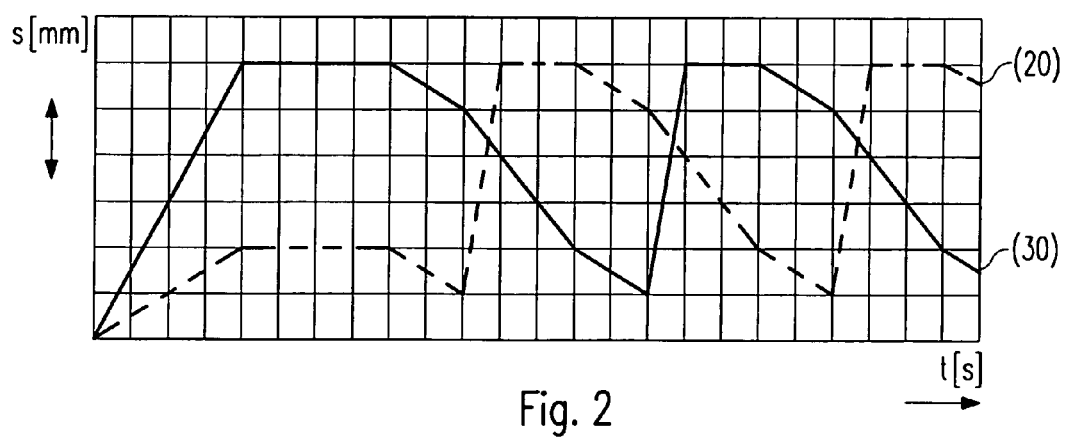
Fig. 1
Fig. 2

TRANSPORT DEVICE FOR STERILE MEDIA

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The invention relates to a device for transporting sterile fluids, e.g. Ringer solution, such as are employed for example in water-jet surgery.

BACKGROUND OF THE INVENTION

In the area of water-jet surgery—this is an especially important example —in general the following requirements must be met:
  The sterility of the fluid must be ensured, because it not only comes into contact with a patient's body but also to some extent remains in the body;
  the required flow and/or the pressure needed for such flow must be substantially constant and reproducibly adjustable, to achieve a reproducible effect on the tissue;
  the person operating the device must be free to select the duration of an individual activation with constant flow;
  containers for the fluid should be available in differing sizes, so that for a particular application the amount required can be kept in reserve, with no need to exchange the container during an application on one hand and, on the other hand, without leaving a too-large container only partially emptied;
  it must be possible to begin and end the activation of the instrument substantially without delay, i.e. the pressure must build up rapidly and no drops may appear post-activity;
  it must be possible to exchange applicators with no problems.

Surgical water-jet cutting devices and associated systems for pressure build-up are known per se. One technical solution to the problem of keeping the operating fluid completely sterile, namely by preventing it from coming into any contact with parts of the pump mechanism, is disclosed by the document DE 42 00 976 C2. With this known solution, however, the user has available only a specific quantity of the fluid medium, because it is contained in a previously prepared cartridge. Once this has been opened, any content that remains cannot be put to further use, regardless of how much or how little has been extracted during the actual operation. The residue must be discarded. The maximal size of the reservoir in this known arrangement is crucially determined by the dimensions of the device. When a small device is desired, it can easily happen that the reservoir must be exchanged during the operation, which constitutes a disturbing interruption of the procedure. Furthermore, the reservoir must be pressurized as a whole, so that there is a dependence on the sizes that are available for the reservoir.

Sterile filters, which allow nonsterile transport in that they filter out any germs that could have entered the cutting medium from a nonsterile transport device, present various disadvantages. One is that the effort of maintenance is considerably increased, because the filters must be exchanged at specified time intervals. Furthermore, filters tend to inhibit the flow behavior. In the case of high pressures, inserted sterile filters are suitable only with some restrictions, because when the instrument is turned on and off they are subjected to major changes in flow and thus also interfere with the required rapid pressure build-up.

BRIEF SUMMARY OF THE INVENTION

It is an object of the invention to provide a transport device for sterile fluids that simplifies and improves its usability in the operating theater over conventionally used devices.

According to the present invention there is provided a transport device for sterile fluids to transport a sterile medium from a reservoir or similar source to a surgical instrument, in particular an instrument for water-jet surgery or a similar consumer apparatus, which comprises a piston pump or similar volumetrically transporting pump, with a suction cycle to draw the medium in and an output cycle to eject the medium, and which furthermore comprises conduits and valve means to connect the pump to the source and to the consumer, as well as drive means to drive the pump, the drive means being constructed and connected to the pump in such a way that the suction cycle is shorter than the output cycle. Alternatively, the pump can comprise three or more pump chambers, which are actuated in such a way that the pump cycles overlap.

In the case of the first alternative the pump preferably comprises at least one first and one second piston/cylinder unit or similar pump chambers, which can be controlled in a push-pull manner so that the suction cycle in the first pump chamber is shorter than the output cycle in the second pump chamber, and conversely. As a result, only two pump chambers suffice to ensure production of a continuous flow.

The drive means are preferably constructed such that the output cycles overlap one another. This ensures an especially uniform flow, with no need for storage vessels or the like.

Each drive means is preferably constructed such that the medium is supplied to the consumer with a substantially constant pressure and hence a constant transported amount. This considerably enhances usability.

Preferably the pump is releasably connected to the drive means. As a result a "sterile device part" can be separated from an "unsterile device part" that could only be sterilized with extreme effort.

In this embodiment it is especially advantageous for the pump and/or the conduits to be constructed, preferably together with the valve means, as a "disposable unit". Thus for each application a "set" consisting of pumps, the conduits and the necessary valve means is connected on one hand to the reservoir for the medium to be transported and on the other hand to the surgical instrument, and is then coupled to the drive means. After use this set as a whole is discarded. In this way complete sterility can be ensured along with simple manipulation, because the set can be sterilized by the manufacturer in a simple manner.

For the drive means various alternatives are possible. For instance, for each pump chamber a separately controllable drive motor can be provided, so that the velocity profile for the individual pump chambers can be set as desired with little effort, by employing an appropriate electronic control system (e.g., by using stepping motors). Alternatively (but in some cases also in addition) the drive means can be provided as gear mechanisms, with a gear train connected to the drive motor and a gear-train output for each pump chamber. Although in this case the ratio of suction cycle to output cycle cannot be changed, the transport rate can be set very easily. The complexity involved here is likewise relatively slight.

Preferred embodiments of the invention are now described by way of example with reference to the accompanying drawings.

BRIEF DESCRIPTION OF THE DRAWINGS

FIG. 1 is a schematic drawing of a first embodiment of the invention,

FIG. 2 is a diagram to explain the pump cycles,

DETAILED DESCRIPTION OF THE INVENTION

Figure 3:
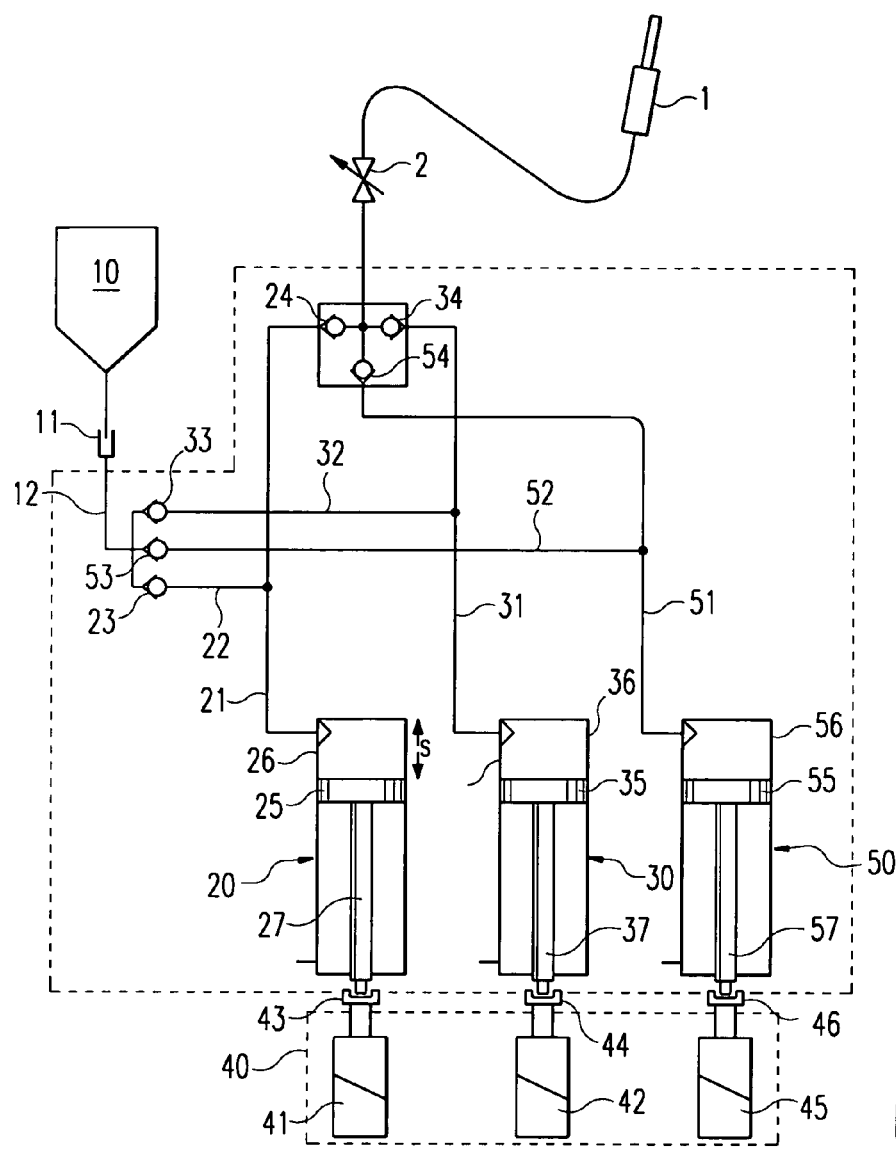
FIG. 3 shows another embodiment of the invention in a drawing similar to FIG. 1.

In the following description, the same reference numerals are used for identical parts or parts with identical actions.

In the embodiment shown in FIG. 1 there are provided a first pump 20 and a second pump 30, each of which comprises a piston 25; 35, a cylinder 26; 36, a piston rod 27; 37, and a pump conduit 21 or 31 connected to a surgical instrument 1 by way of output valves 24 and 34, respectively, and a clamp valve 2.

The pump conduits 21 and 31 are connected by way of suction conduits 22 and 32 and suction valves 23 and 33 to a suction conduit 12 that can be connected to a source 10 by way of a releasable coupling 11.

The piston rods 27 and 37 are releasably connected, by way of a first coupling 43 and second coupling 44, respectively, to a first motor 41 and second motor 42. The parts enclosed by the dashed line in FIG. 1 constitute a disposable unit, which is sterilized and placed in sterile packaging by the manufacturer and is sent in this form to the merchant and/or end user.

The drive motors 41, 42 are connected to a control means (not shown) that controls the drive motors 41, 42 in such a way that the pistons 25, 35 travel along a path s, the time course of which is illustrated in FIG. 2. As shown in FIG. 2, the suction cycles, during which the quantity s increases (so that the curves for s rise in FIG. 2), are much shorter than the output cycles (during which the curves in FIG. 2 are falling). Furthermore, the output cycles overlap in such a way that the sum of the volumes (defined by the pistons 25 and 35 as well as the cylinders 26 and 36) per unit time remains the same, with no decrease, so that a constant outflow of liquid from the source 10 to the surgical instrument 1 is ensured. As customary values for the pressure during employment in water-jet surgery, ca. 20 to 100 bar can be cited. Preferred stroke volumes of the pumps 20, 30 are between 2 and 100 ml per stroke.

The embodiment of the invention shown in FIG. 3 differs from that according to FIG. 1 primarily in that a third pump 50 with a third pump conduit 51, a third suction conduit 52, a third suction valve 53, a third output valve 54, a third piston 55, a third cylinder 56 and a third piston rod 57 are provided, as well as a third motor 45 and a third coupling 46 connected to the third piston rod 57.

Figure 4:
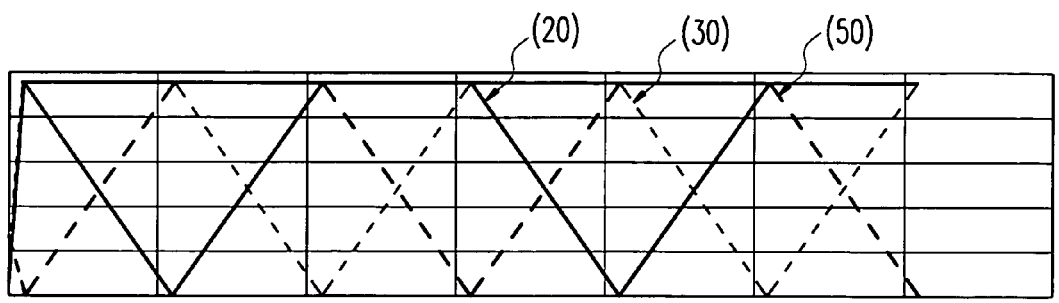
FIG. 4 is a diagram to explain the pump cycles of the arrangement according to FIG. 3.

In addition, in this embodiment of the invention the control means (not shown here) for the motors 41, 42 and 45 can be constructed so that the suction cycles are exactly as long as the output cycles, in which case the three cycles are arranged to be overlapping in such a way that again a uniform pump output, i.e. pumped volume per unit time, is ensured. This is indicated schematically in FIG. 4, where the curves for the individual pumps 20, 30 and 50 are identified by these reference numerals.

Figure 5:
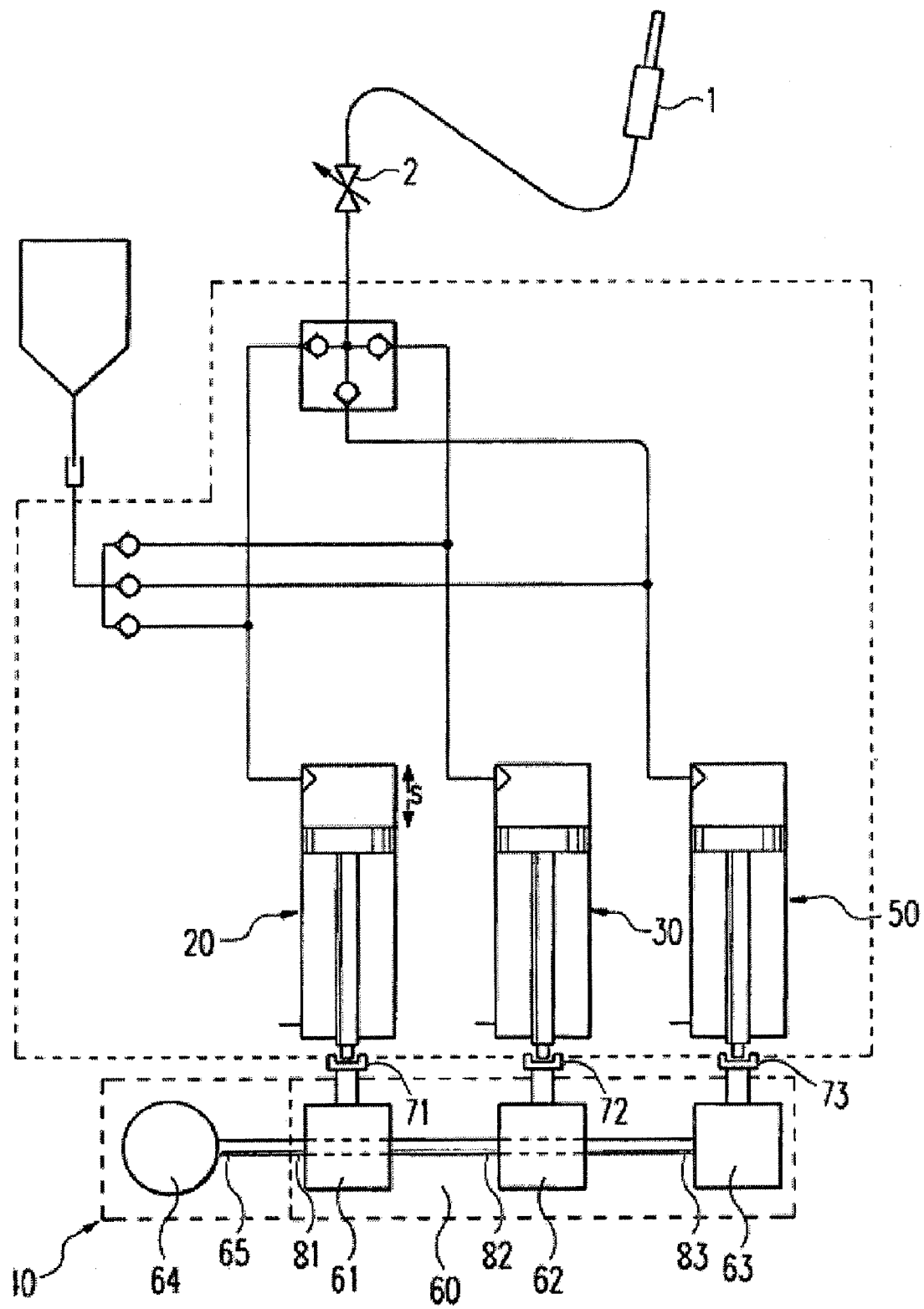
FIG. 5 shows a third preferred embodiment of the invention.

The additional embodiment of the invention shown in FIG. 5 corresponds to the one in FIG. 3 except that no separate pump motors 41, 42 and 45 are provided. Instead the drive means 40 comprises a single motor 64, the shaft 65 of which is connected to a gear arrangement 60 comprising three gear mechanisms 61, 62 and 63, each of which includes a gear-train input 81, 82, and 83 connected to the motor 64 and a gear-train output 71, 72, and 73, which drives a pump 20, 30 and 50, respectively. The gear mechanisms 61, 62 and 63 can be constructed, for example, as disk cam mechanisms, so that the actuation cycles can be arranged similarly to those according to FIG. 4. It is of course also possible to use a drive means 40 designed in this way with the embodiment according to FIG. 1.

LIST OF REFERENCE NUMERALS

1 Surgical instrument
2 Clamp valve
10 Source
11 Coupling
12 Suction conduit
20 1st pump
21 1st pump conduit
22 1st suction conduit
23 1st suction valve
24 1st output valve
25 1st piston
26 1st cylinder
27 1st piston rod
30 2nd pump
31 2nd pump conduit
32 2nd suction conduit
33 2nd suction valve
34 2nd output valve
35 2nd piston
36 2nd cylinder
37 2nd piston rod
40 Drive means
41 1st motor
42 2nd motor
43 1st coupling
44 2nd coupling
45 3rd motor
46 3rd coupling
50 3rd pump
51 3rd pump conduit
52 3rd suction conduit
53 3rd suction valve
54 3rd output valve
55 3rd piston
56 3rd cylinder
57 3rd piston rod
60 Gear arrangement
61 1st part of gear arrangement
62 2nd part of gear arrangement
63 3rd part of gear arrangement
64 Motor
65 Shaft

The invention claimed is:

1. A surgical fluid pump system for transporting a sterile fluid from a source to a surgical instrument, comprising:
a drive system; and
a pump system comprising:
an inlet for establishing a fluid connection to said source;
an outlet for establishing a fluid connection to said surgical instrument;
first and second pumps, each of said first and second pumps comprises a pump conduit connectable to the surgical instrument by way of output valves, wherein the pump conduits are connected by way of suction conduits and suction valves to a common suction conduit that can be connected to the source by way of a releasable coupling;
each of said first and second pumps having a piston that contacts said sterile fluid to apply a pressure to said sterile fluid, each of said pumps having a suction cycle for drawing in the sterile fluid and an output cycle for ejecting the sterile fluid, wherein a separately controllable drive motor is provided for each of said first and second pumps; and
an electronic control system for controlling the drive motors by setting a piston velocity profile for each of the first and second pumps;
wherein the pump system is releasably connected to the drive system, and
said drive system drives said pump system in such a way that said suction cycle of each pump is shorter than said output cycle of each pump and in such a way that the output cycles of the first and second pumps overlap so that said fluid is supplied to said outlet with a substantially constant pressure.

2. The surgical fluid pump system according to claim 1, wherein
said drive system drives said first and second pumps in a push-pull manner in such a way that the suction cycle in the first pump is shorter than the output cycle in the second pump and that the suction cycle in the second pump is shorter than the output cycle in the first pump.

3. The surgical fluid pump system according to claim 1, wherein said drive system drives said pump system in such a way that said output cycles overlap.

4. A surgical fluid pump system for transporting a sterile fluid from a source to a surgical instrument, said system comprising:
a drive system; and
a disposable pump system comprising:
an inlet for establishing a fluid connection to said source;
an outlet for establishing a fluid connection to said surgical instrument;
first, second and third pumps, each of said first, second and third pumps comprises a pump conduit connectable to the surgical instrument by way of output valves, wherein the pump conduits are connected by way of suction conduits and suction valves to a common suction conduit that can be connected to the source by way of a releasable coupling;
each of the three pumps having a piston that contacts said sterile fluid to apply a pressure to said sterile fluid, each of said pumps having a suction cycle for drawing in the sterile fluid and an output cycle for ejecting the sterile fluid, wherein a separately controllable drive motor is provided for each of said three pumps; and
an electronic control system for controlling the drive motors by setting a piston velocity profile for each of the three pumps;
wherein the pump system is releasably connected to the drive system, and
said drive system drives said pump system in such a way that the suction cycle of one or more of the pumps overlap with the output cycle of one or more of the remaining pumps.

5. The surgical fluid pump system according to claim 4, wherein
said drive system comprises a controllable rotary drive motor configured and adapted to mechanically drive said piston of each of said pumps.

6. The surgical fluid pump system according to claim 4, wherein said drive system drives said pump system in such a way that said output cycles overlap.

7. The surgical fluid pump system according to claim 4, wherein said drive system drives said pump system in such a way that said fluid is supplied to said outlet with a substantially constant pressure.

8. A surgical fluid pump system for transporting a sterile fluid from a source to a surgical instrument, said system comprising:
a drive system; and
a pump system comprising:
an inlet for establishing a fluid connection to said source;
an outlet for establishing a fluid connection to said surgical instrument;
first and second pumps, each of said first and second pumps comprises a pump conduit connectable to the surgical instrument by way of output valves, wherein the pump conduits are connected by way of suction conduits and suction valves to a common suction conduit that can be connected to the source by way of a releasable coupling;
each of said first and second pumps having a piston that contacts said sterile fluid to apply a pressure to said sterile fluid, each of said pumps having a suction cycle for drawing in the sterile fluid and an output cycle for ejecting the sterile fluid, wherein a separately controllable drive motor is provided for each of said first and second pumps; and
an electronic control system for controlling the drive motors by setting a piston velocity profile for each of the first and second pumps;
wherein the drive system drives said pump system in such a way that, for each of said first and second pumps, the suction cycle of said first pump is shorter than the output cycle in the second pump and vice versa and in such a way that the output cycles of the first and second pumps overlap,
the pump system is releasably connected to the drive system, and
said pump system is constructed as a disposable unit.

9. The surgical fluid pump system according to claim 8, wherein said drive system drives said first and second pumps in a push-pull manner in such a way that the suction cycle in the first pump is shorter than the output cycle in the second pump and that the suction cycle in the second pump is shorter than the output cycle in the first pump.

10. The surgical fluid pump system according to claim 8, wherein the drive system drives said pump system in such a way that the fluid is supplied to the outlet with a substantially constant pressure.

11. The surgical fluid pump system according to claim 8, wherein
said drive system comprises a controllable rotary drive motor configured and adapted to mechanically drive said piston of each of said first and second pumps.

12. A surgical fluid pump system for transporting a sterile fluid from a source to a surgical instrument, comprising:
- a drive system; and
- a pump system comprising:
  - an inlet for establishing a fluid connection to said source;
  - an outlet for establishing a fluid connection to said surgical instrument;
  - first, second and third pumps, each of said first, second and third pumps comprises a pump conduit connectable to the surgical instrument by way of output valves, wherein the pump conduits are connected by way of suction conduits and suction valves to a common suction conduit that can be connected to the source by way of a releasable coupling;
  - each of the three pumps having a piston that contacts said sterile fluid to apply a pressure to said sterile fluid, each of said pumps having a suction cycle for drawing in the sterile fluid and an output cycle for ejecting the sterile fluid, wherein a separately controllable drive motor is provided for each of said at least three pumps; and
  - an electronic control system for controlling the drive motors by setting a piston velocity profile for each of the at least three pumps;
  - wherein the pump system is releasably connected to the drive system, and
  - the drive system drives said pump system in such a way that, for each of said at least three pumps, the suction cycle is shorter than the output cycle and in such a way that the suction cycle of one or more of the pumps overlap with the output cycles of one or more of the remaining pumps.

13. The surgical fluid pump system according to claim 12, wherein the drive system drives said pump system in such a way that the output cycles overlap.

14. The surgical fluid pump system according to claim 12, wherein the drive system drives said pump system in such a way that the fluid is supplied to the outlet with a constant pressure.

15. The surgical fluid pump system according to claim 12, wherein the pump system is constructed as a disposable unit.

16. The surgical fluid pump system according to claim 12, wherein said drive system comprises a controllable rotary drive motor configured and adapted to mechanically drive said piston of each of said pumps.

17. A surgical fluid pump system for transporting a sterile fluid from a source to a surgical instrument, said system comprising:
- a drive system; and
- a pump system comprising:
  - an inlet for establishing a fluid connection to said source;
  - an outlet for establishing a fluid connection to said surgical instrument;
  - first, second and third pumps, each of said first, second and third pumps comprises a pump conduit connectable to the surgical instrument by way of output valves, wherein the pump conduits are connected by way of suction conduits and suction valves to a common suction conduit that can be connected to the source by way of a releasable coupling;
  - each of the three pumps having a piston that contacts said sterile fluid to apply a pressure to said sterile fluid, each of said pumps having a suction cycle for drawing in the sterile fluid and an output cycle for ejecting the sterile fluid, wherein a separately controllable drive motor is provided for each of said at least three pumps; and
  - an electronic control system for controlling the drive motors by setting a piston velocity profile for each of the at least three pumps;
  - wherein the pump system is releasably connected to the drive system, and
  - the drive system drives said pump system in such a way that the suction cycle of one or more of the pumps overlap with the output cycle of one or more of the remaining pumps.

18. The surgical fluid pump system according to claim 17, wherein the drive system drives said pump system in such a way that the fluid is supplied to the outlet with a constant pressure.

19. The surgical fluid pump system according to claim 17, wherein the pump system is constructed as a disposable unit.

20. The surgical fluid pump system according to claim 17, said drive system comprises a controllable rotary drive motor configured and adapted to mechanically drive said piston of each of said pumps.

21. A disposable surgical fluid pumping device for pumping a sterile fluid from a source to a surgical instrument, comprising:
- an inlet for establishing a fluid connection to said source;
- an outlet for establishing a fluid connection to said surgical instrument;
- a plurality of pumps, each of said plurality of pumps comprises a pump conduit connectable to the surgical instrument by way of output valves, wherein the pump conduits are connected by way of suction conduits and suction valves to a common suction conduit that can be connected to the source by way of a releasable coupling;
- each of said pumps including a piston that contacts said sterile fluid to apply a pressure to said sterile fluid, wherein a separately controllable drive motor is provided for each of said plurality of pumps; and
- an electronic control system for controlling the drive motors by setting a piston velocity profile for each of the plurality of pumps;
- wherein said valve devices prohibit an outflow of said sterile fluid at said inlet and prohibit an inflow of said sterile fluid at said outlet, and
- a portion of said sterile fluid path from said inlet to a respective one of said pumps is common to a portion of said sterile fluid path from said respective one of said pumps to said outlet.

* * * * *